(12) United States Patent
ElAttrache et al.

(10) Patent No.: US 6,544,281 B2
(45) Date of Patent: Apr. 8, 2003

(54) GRAFT FIXATION USING A SCREW OR PLUG AGAINST SUTURE OR TISSUE

(75) Inventors: Neal ElAttrache, Playa del Ray, CA (US); Stephen S. Burkhart, San Antonio, TX (US); Peter Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 09/886,280

(22) Filed: Jun. 22, 2001

(65) Prior Publication Data

US 2002/0013608 A1 Jan. 31, 2002

Related U.S. Application Data

(60) Provisional application No. 60/213,263, filed on Jun. 22, 2000.

(51) Int. Cl.[7] ............................................... A61B 17/04
(52) U.S. Cl. ..................................................... 606/232
(58) Field of Search ................................. 606/232, 104

(56) References Cited

U.S. PATENT DOCUMENTS

| | | | |
|---|---|---|---|
| 4,784,126 A | * 11/1988 | Hourahane | 606/60 |
| 5,152,790 A | * 10/1992 | Rosenberg et al. | 606/73 |
| 5,380,334 A | 1/1995 | Torrie et al. | |
| 5,645,547 A | 7/1997 | Coleman | |
| 5,702,398 A | 12/1997 | Tarabishy | |
| 6,036,694 A | * 3/2000 | Goble et al. | 606/72 |

* cited by examiner

Primary Examiner—Gary Jackson
(74) Attorney, Agent, or Firm—Dickstein Shapiro Morin & Oshinsky, LLP

(57) ABSTRACT

A method for securing soft tissue to bone with excellent pull-out strength which does not require the surgeon to tie suture knots to secure the tissue to the bone. A blind hole or socket is created in the bone at the location the graft is to be secured. Preferably, suture is then passed through the graft at desired points. A cannulated driver is pre-loaded with a cannulated plug or screw slidably disposed onto the distal portion of the driver. In a preferred embodiment, a separate piece of suture is passed through the cannula of the driver with a loop end of that suture exposed at the distal end of the driver. The ends of the suture attached to the graft are fed through the suture loop at the end of the driver. Alternatively, the graft itself may be fed through the suture loop, in which case it is not necessary to attach suture through the graft. In another embodiment, the suture loop exposed at the distal end of the cannula of the driver may be omitted, and the sutures attached to the graft may then be fed through the driver cannula from the distal end to position the graft relative to the driver. The driver is inserted into the hole with the screw or plug just outside the hole. Tension is then placed on the suture. Once adequate tension is achieved on the suture, the driver is pressed into the hole, which engages the first thread or bump of the screw or plug on the bone. The screw or plug is then fully advanced into the hole using the driver. When the screw or plug is fully inserted, the suture loop is freed and the driver is removed. The loose ends of the sutures protruding from the anchor site can be cleaned up by clipping them short.

20 Claims, 14 Drawing Sheets

GRAFT FIXATION USING A SCREW OR PLUG AGAINST SUTURE OR TISSUE

This application claims the benefit of U.S. Provisional Application Ser. No. 60/213,263 filed Jun. 22, 2000.

BACKGROUND OF THE INVENTION

1. Field of the Invention

The present invention relates to methods and apparatus for fixation of sutures and soft tissue to bone using a screw or plug.

2. Description of the Related Art

When soft tissue such as a ligament or a tendon becomes detached from a bone, surgery is usually required to reattach or reconstruct the tissue. Often, a tissue graft is attached to the bone to facilitate regrowth and permanent attachment. Various fixation devices, including sutures, screws, staples, wedges, and plugs have been used in the past to secure soft tissue to bone. In typical interference screw fixation, for example, the graft is fixed to the bone by driving the screw into a blind hole or a tunnel in the bone while trapping the end of the graft between the screw and the bone tunnel. In other methods, the graft is simply pinned against the bone using staples or sutures tied around the end of the graft to the bone.

More recently, various types of threaded suture anchors have been developed. The application of such suture anchors generally requires the surgeon to tie knots in the suture to secure the tissue to the bone, which is tedious and time-consuming. The surgical procedure would be less cumbersome for the surgeon and ultimately more beneficial to the patient if the tissue could be attached to the bone without the surgeon having to tie suture knots.

SUMMARY OF THE INVENTION

The present invention provides a surgical technique and associated device for securing soft tissue to bone with excellent pull-out strength and which does not require the surgeon to tie suture knots to secure the tissue to the bone. The present invention may be used to secure any type of soft tissue, graft, or tendon, such as, for example, a biceps tendon or a rotator cuff.

In a preferred embodiment of the invention, a blind hole or socket is created in the bone at the location that the graft is to be secured. Suture is passed through the graft at desired points. A cannulated plug or screw is pre-loaded onto the distal end of a cannulated driver. In a preferred embodiment, a separate piece of suture is passed through the cannula of the driver, with a looped end of the suture exposed at the distal end of the driver. The ends of the suture attached to the graft are fed through the suture loop at the end of the driver. Tension is placed on the suture to bring the graft to an appropriate distance from the distal end of the driver. Here, the graft is either brought to the distal end of the driver or spaced away from the distal end of the driver by a distance approximately equal to the length of the screw or plug. The distal end of the driver is inserted into the bottom of the hole, with the screw or plug disposed just outside the hole. Once adequate tension is achieved on the suture to keep the graft at the desired location relative to the bone hole and the distal end of the plug or screw, the driver is pressed into the hole, engaging the first thread or bump of the screw or plug. The screw or plug is then fully advanced into the hole using the driver to frictionally secure either the suture attached to the graft or the graft itself into the bone hole. When the screw or plug is fully inserted, the suture loop is freed and the driver is removed. The loose ends of the sutures protruding from the anchor site are then clipped short.

Alternatively, the step of passing suture through the graft may be omitted, so that the graft itself is captured in the suture loop to be directly affixed into the fixation hole.

In another alternative, the suture loop through the driver may be omitted, and the graft is positioned relative to the driver by inserting the ends of the suture attached to the graft into and through the cannula of the driver from the distal end thereof.

Other features and advantages of the present invention will become apparent from the following description of the invention which refers to the accompanying drawings.

DETAILED DESCRIPTION OF THE PREFERRED EMBODIMENTS

Figure 1:
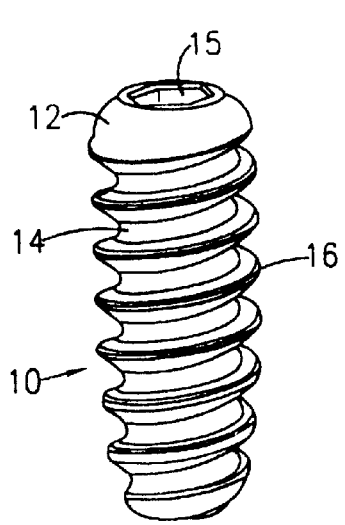
FIG. 1 illustrates a proximal end, side elevational view of an embodiment of an interference screw to be used with the present invention.
Figure 2:
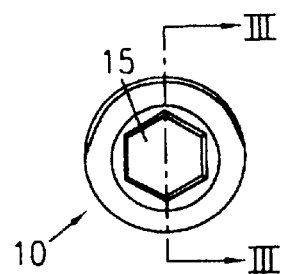
FIG. 2 is a proximal end view of the screw shown in FIG. 1.
Figure 3:
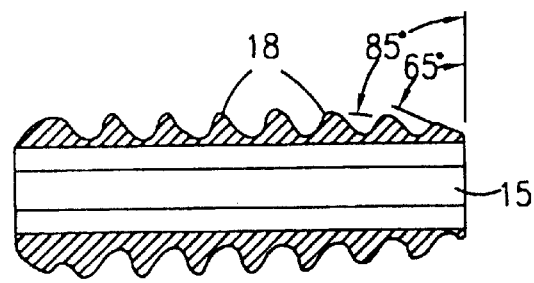
FIG. 3 is a cross-sectional view, drawn along line III—III of FIG. 2, of the screw shown in FIG. 1.

Referring to FIGS. 1–3, an interference screw 10 according to the present invention is shown. Screw 10 is preferably formed of a bioabsorbable material such as PLLA and has a cannulated body 12 provided with a continuous thread 16 having rounded outer edges 18. The head of the screw 14 is rounded to minimize abrasion or cutting of tissue, and the screw tapers toward the distal end. A hexagonal bore 15 formed through the screw accepts a driver shaft described in more detail below.

Figure 4:
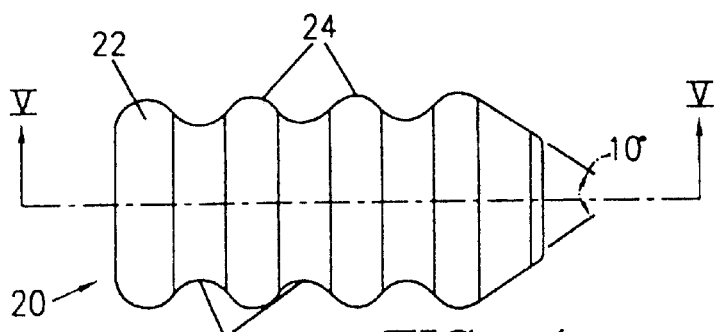
FIG. 4 illustrates a side elevational view of an embodiment of an interference plug according to the present invention.
Figure 5:
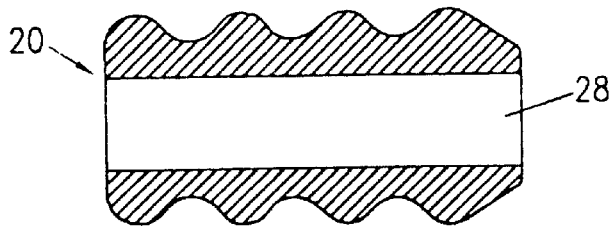
FIG. 5 is a cross-sectional view of the plug shown in FIG. 4.
Figure 6:
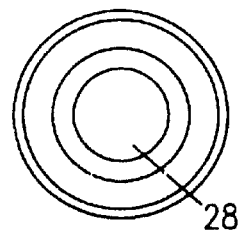
FIG. 6 is a distal end view of the plug shown in FIG. 6.

FIGS. 4–6 illustrate an interference plug 20 according to an alternative embodiment of the present invention. Plug 20 is also preferably formed of a bioabsorbable material and has a cannulated body 22 provided with rounded annular ribs 24 separated by rounded annular grooves 26. The outer diameter of the ribs and grooves is substantially constant. The plug tapers significantly toward the distal end. Cannula 28 is preferably round in cross-section but may also be hexagonal or any other shape, and is designed to accommodate the shaft of a corresponding driver.

Figure 7:
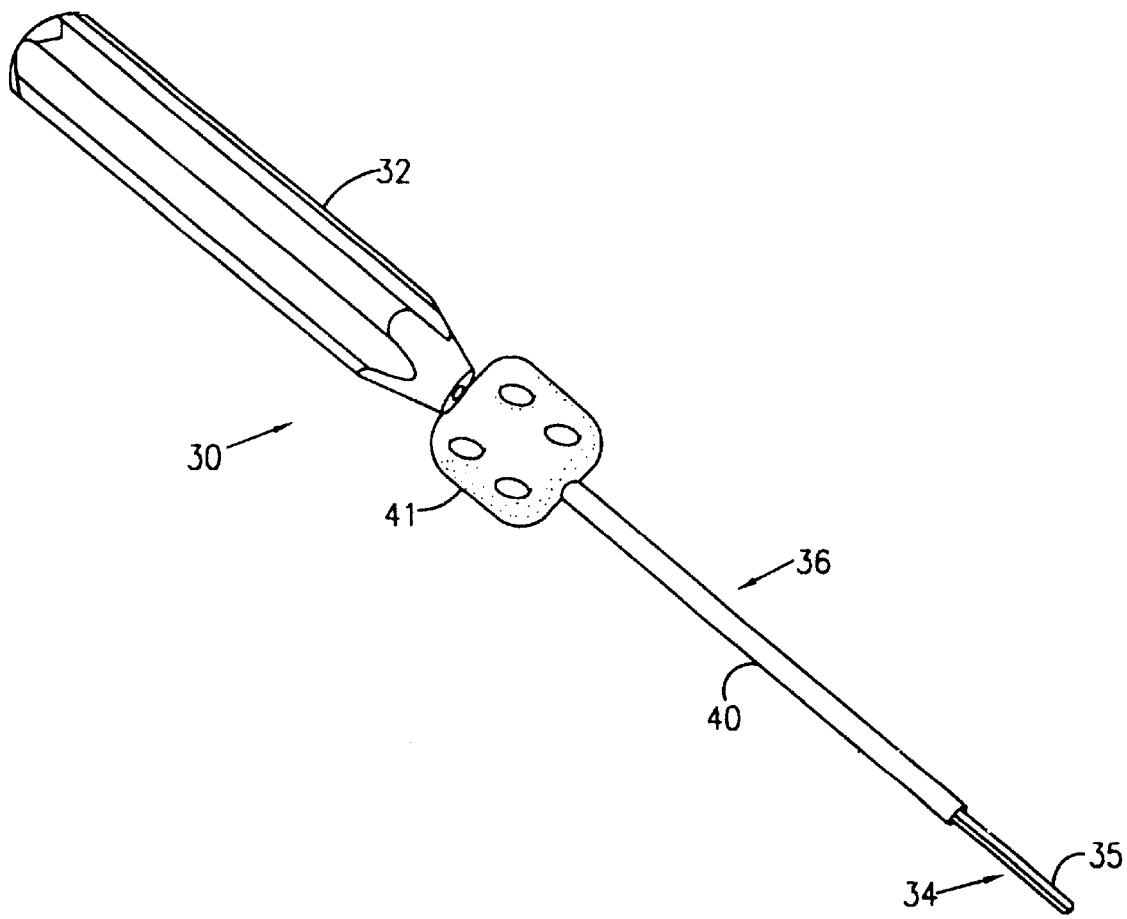
FIG. 7 illustrates a driver according to the present invention for driving the interference screw shown in FIG. 1.
Figure 8:
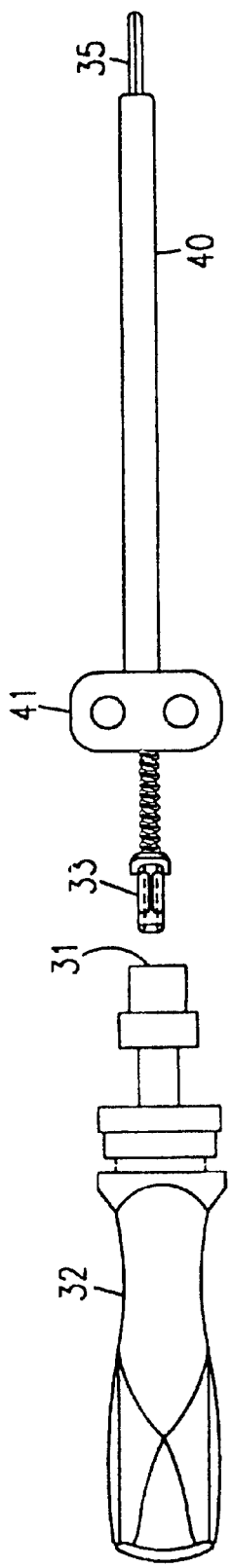
FIG. 8 shows a handle according to a variation of the driver seen in FIG. 7.

FIG. 7 illustrates a driver 30 according to the present invention for driving the interference screw described above. Generally, driver 30 includes a handle 32, inner shaft 34, and outer shaft 36. FIG. 8 shows a handle having a connector 31 for coupling with driver 30.

Figure 9:
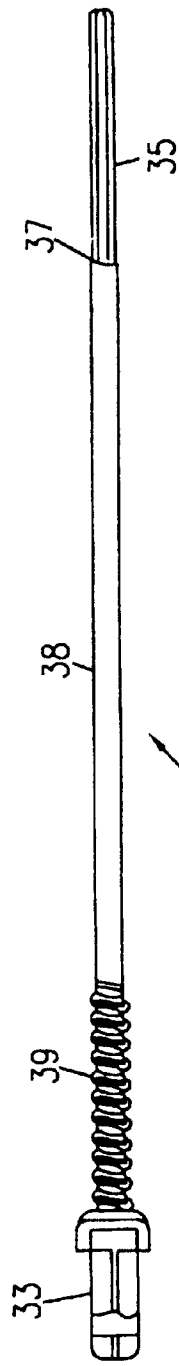
FIG. 9 shows the inner shaft attachable to the driver handle shown in FIG. 8.

FIG. 9 shows the inner shaft of driver 30. Inner shaft 34 has a cannula extending through its entire length and has openings at the proximal and distal ends to enable sutures to be passed therethrough. Inner shaft 34 includes a shaft body 38 having a threaded proximal section 39 and a hex-shaped distal section 35 for being fitted through the cannula 15 in interference screw 10. The diameter of the shaft body 38 is reduced slightly along the hex section 35, forming a shoulder 37 at the junction between the hex section 35 and the central portion of shaft body 38 for abutting the proximal end of an interference screw loaded onto the driver. Shaft 34 can be permanently affixed to the handle 32 as shown in FIG. 7, or can be releasably attached, as shown in the embodiment represented in FIGS. 8 and 9, by means of a collet 33 at the proximal end of the threaded section 39 being fittable within a connector 31 at the distal end of handle 32.

Figure 10:
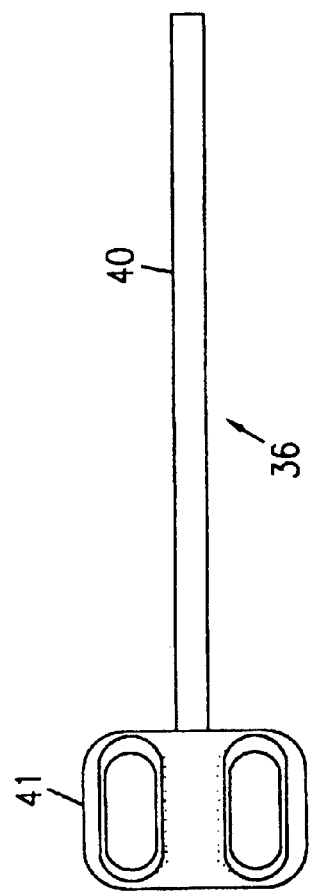
FIG. 10 shows the outer shaft of the driver according to the present invention.

FIG. 10 shows the outer shaft 36 of the driver 30. Outer shaft 36 includes a sleeve 40 which covers and is slidable over shaft body 38, and a thumb pad 41 for being gripped by a user. Outer shaft 36 is cannulated through its entire length, of course, with the diameter of the cannula being slightly larger than the outer diameter of the central portion of inner shaft body 38. The portion of the cannula through thumb pad 41 is threaded to mate with the threads on the threaded proximal section 39 on inner shaft 34. The inner diameter of the inner threads in thumb pad 41 is smaller than the outer diameter of the central portion of shaft body 38, so as to limit the proximal movement of the outer shaft 36 relative to the inner shaft 34.

The proximal threaded section 39 on the inner shaft 34 has a length such that when the outer shaft 36 is unscrewed to its proximal-most position with the thumbpad adjacent the distal end of handle 32 or connector 31, shoulder 37 on the inner shaft 34 is flush with or exposed through the distal end of sleeve 40 of outer shaft 36.

The length of hex section 35 is such that when a cannulated interference screw is loaded onto the driver with the proximal end of the screw abutting the shoulder 37, the hex driver portion exposed distally of the mounted screw can reach the bottom of a socket created in the bone where the screw will be inserted, while the screw is positioned just outside the hole. Thus, the hex section 35 has a length which is approximately twice the length of the interference screw usable with the driver. Similarly, the length of the threaded proximal section 39 is also approximately equal to the length of the screw.

Figure 11:
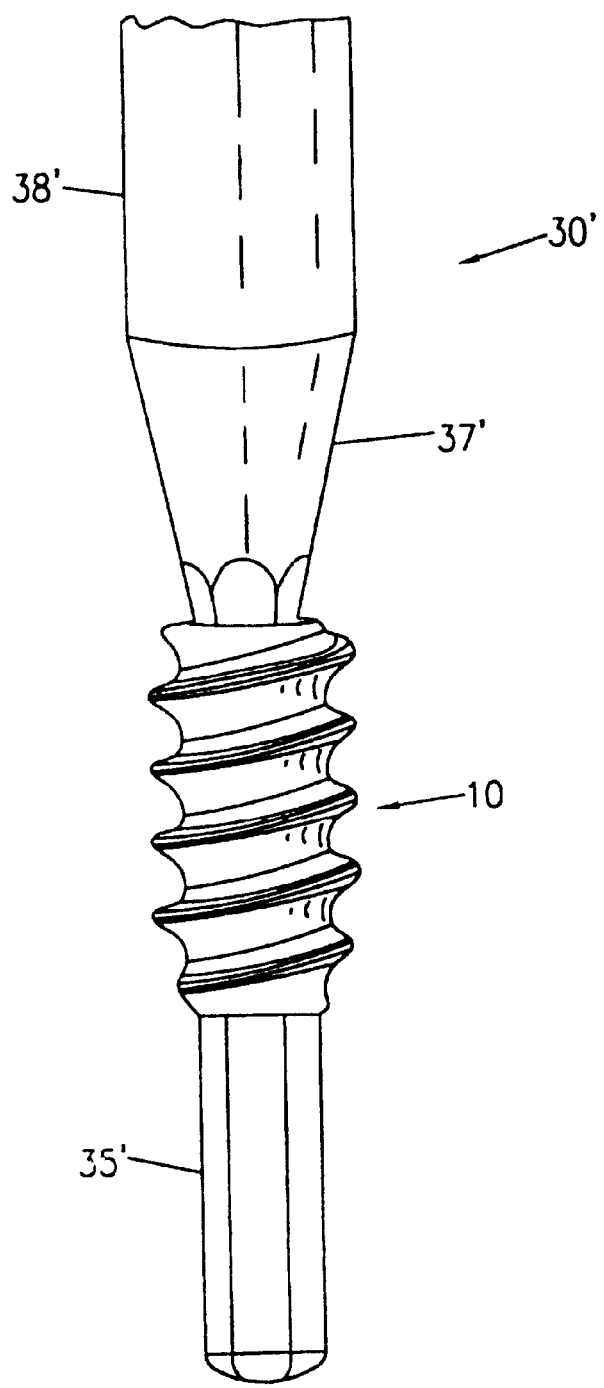
FIG. 11 illustrates an alternative embodiment of a driver for driving an interference screw, together with a screw loaded thereon.

An alternative embodiment of the driver for the interference screw is shown in FIG. 11. In this embodiment, the outer shaft is eliminated so that the driver 30' is comprised of a single cannulated shaft. The shaft body 38' has an enlarged outer diameter relative to that of the previous embodiment, and tapers down to hex section 35' via a tapered section 37'. When loading a screw onto the driver 30', the proper initial position of the screw is established by inserting the hex section through the cannula of the screw until the travel of the proximal end of the screw 10 is limited by the increased diameter in tapered section 37'. As before, the hex section has a length which enables the distal end of the hex section to be inserted to the bottom of the socket while positioning an intereference screw loaded onto the driver just outside the socket with the bottom thread of the screw able to engage the opening of the hole upon the application of a small amount of force into the hole.

Figure 12A:
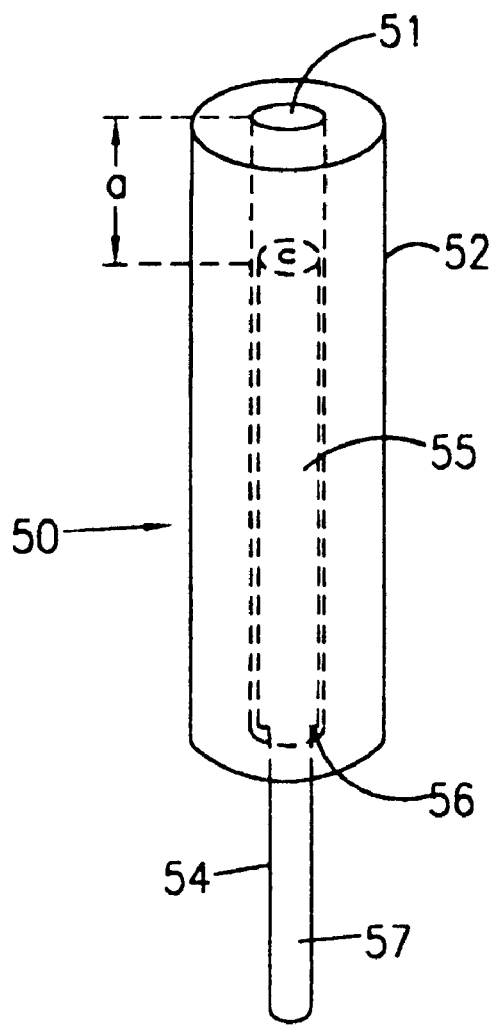
FIGS. 12A and 12A illustrate a driver according to the present invention usable for the interference plug shown in FIG. 4.
Figure 12B:
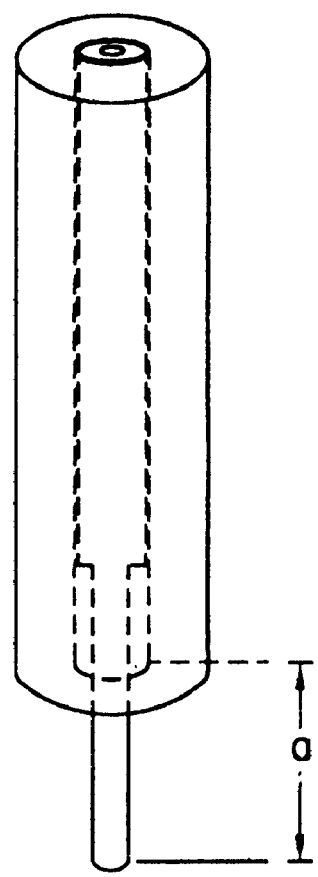

FIGS. 12A and 12B illustrate an example of a driver usable with an interference plug in accordance with the present invention, in which the plug is driven into the socket by impaction rather than being screwed into place. Driver 50 comprises essentially of an outer shaft 52 and a cannulated inner shaft 54. Inner shaft 54 is inserted into the cannula 51 of outer shaft 52 and has a proximal portion 55 which has an outer diameter slightly smaller than the diameter of cannula 51 to enable the outer shaft 52 to slide along proximal portion 55. Inner shaft 54 also has a distal portion 57 which has a diameter smaller than that of proximal portion 55 and sized for insertion into the cannula 28 of interference plug 20. The cross-sectional shape of distal portion 57, and hence of cannula 28 of plug 20, is preferably round, but can also be hex or any other shape, as long as the distal portion 57 of inner shaft 54 is matingly shaped with the distal portion 57 of driver 50 to be insertable into cannula 28 of plug 20. The junction between proximal portion 55 and distal portion 57 forms shoulder 56 for abutting the proximal end of the plug when the plug is loaded onto the driver 50.

The length of outer shaft 52 is equal to the length of proximal portion 55 of inner shaft 54 plus a distance "a" equal to the length of the interference plug usable therewith. The length of distal section 57 is approximately equal to twice the length of a plug 20, and shoulder 56 on the inner shaft 54 is flush with or just exposed through the distal end of outer shaft 52 when outer shaft 52 is in its fully retracted (proximal) position.

A method of performing soft tissue fixation in accordance with a preferred embodiment of the present invention will now be described with reference to FIGS. 14–19.

Figure 13:
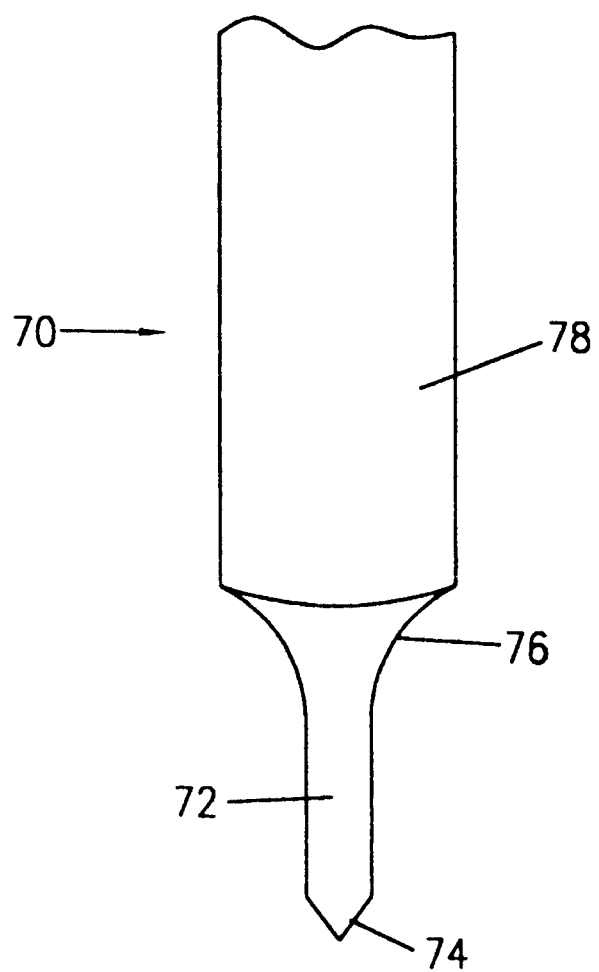
FIG. 13 illustrates a punch usable in connection with the present invention to create a bone socket for securing the graft.
Figure 14:
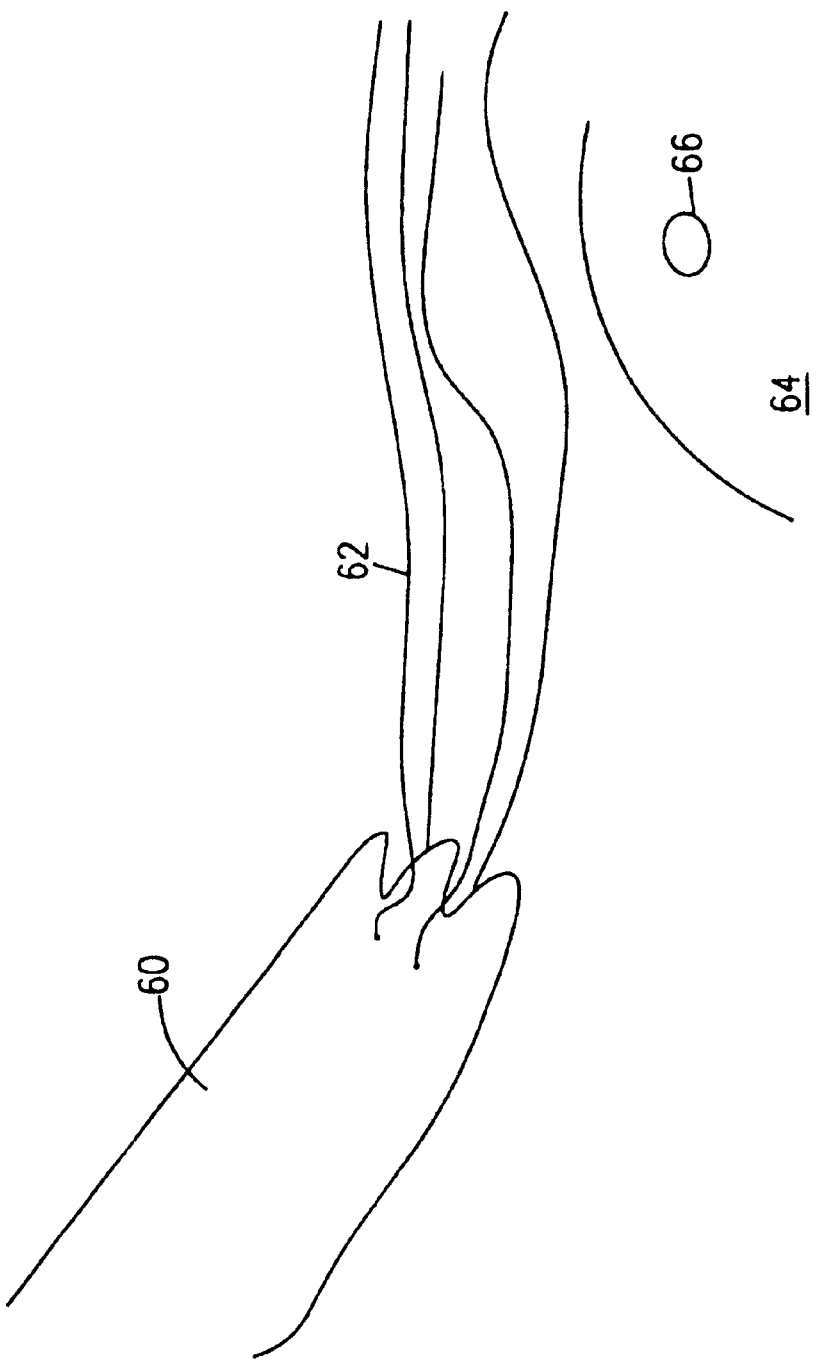
FIG. 14 illustrates a graft to be secured to the bone with attached sutures, and a socket created in the bone at the location at which the graft is to be affixed.

As shown in FIG. 14, sutures 62 are passed through the graft 60 at desired points, and a blind hole or socket 66 is created in the bone 64, using a drill or punch, at the location where the tissue is to be secured. A punch provides the advantages of rounding the opening edge of the bone socket to protect the sutures attached to the graft from being sheared during the insertion process, and also compacts the bone at the punch site for better purchase of the bone by the anchor in cases where the bone is a soft bone. An example of such a punch is illustrated in FIG. 13, the punch having a constant diameter section 72, a tip 74, a flared section 76, and a main body portion 78. The diameter of the constant diameter section corresponds to the diameter of the driver.

Figure 15:
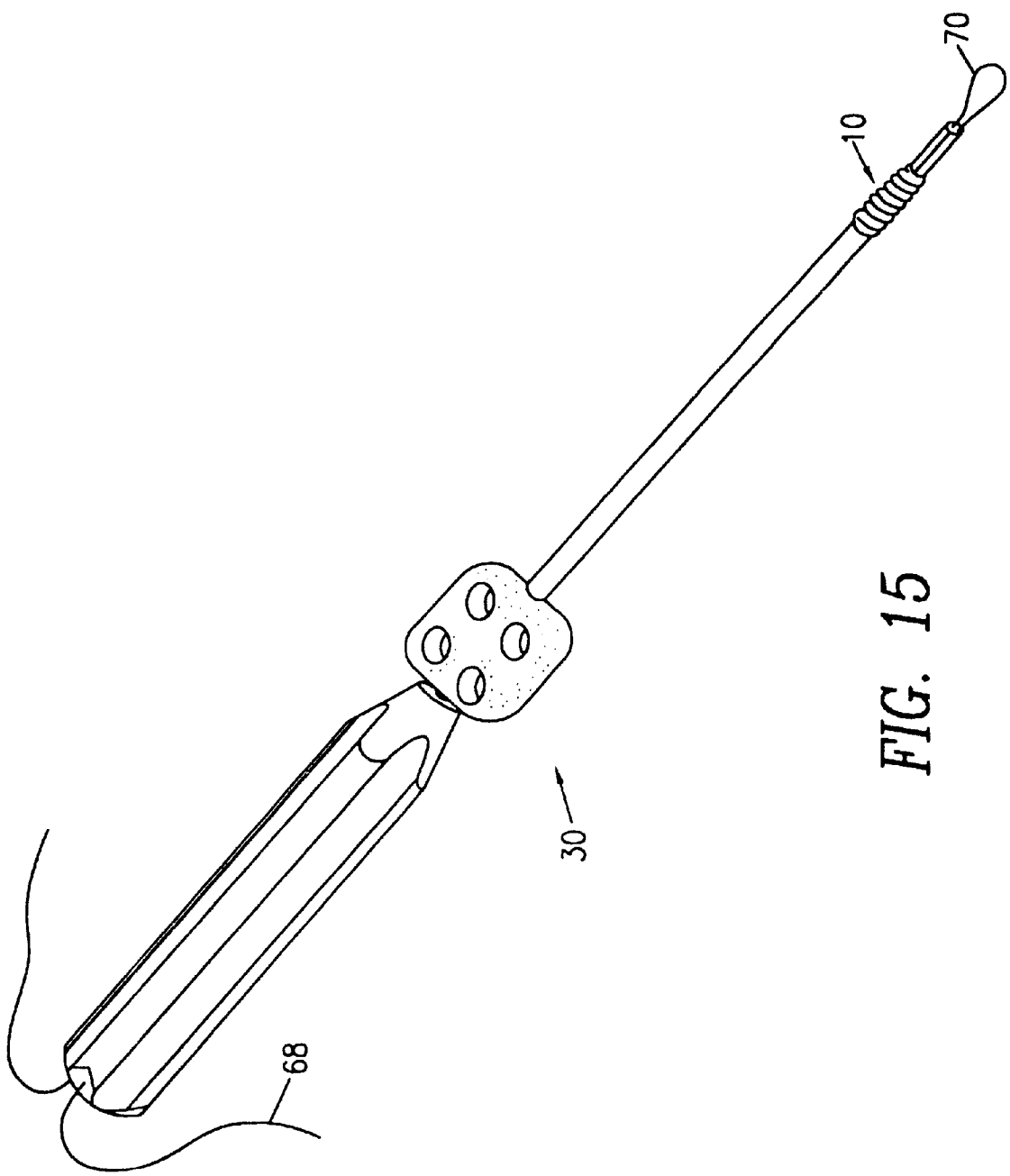
FIG. 15 shows the driver of FIG. 7 loaded with an interference screw and having a traction suture loop formed at the distal end of the driver.
Figure 16:
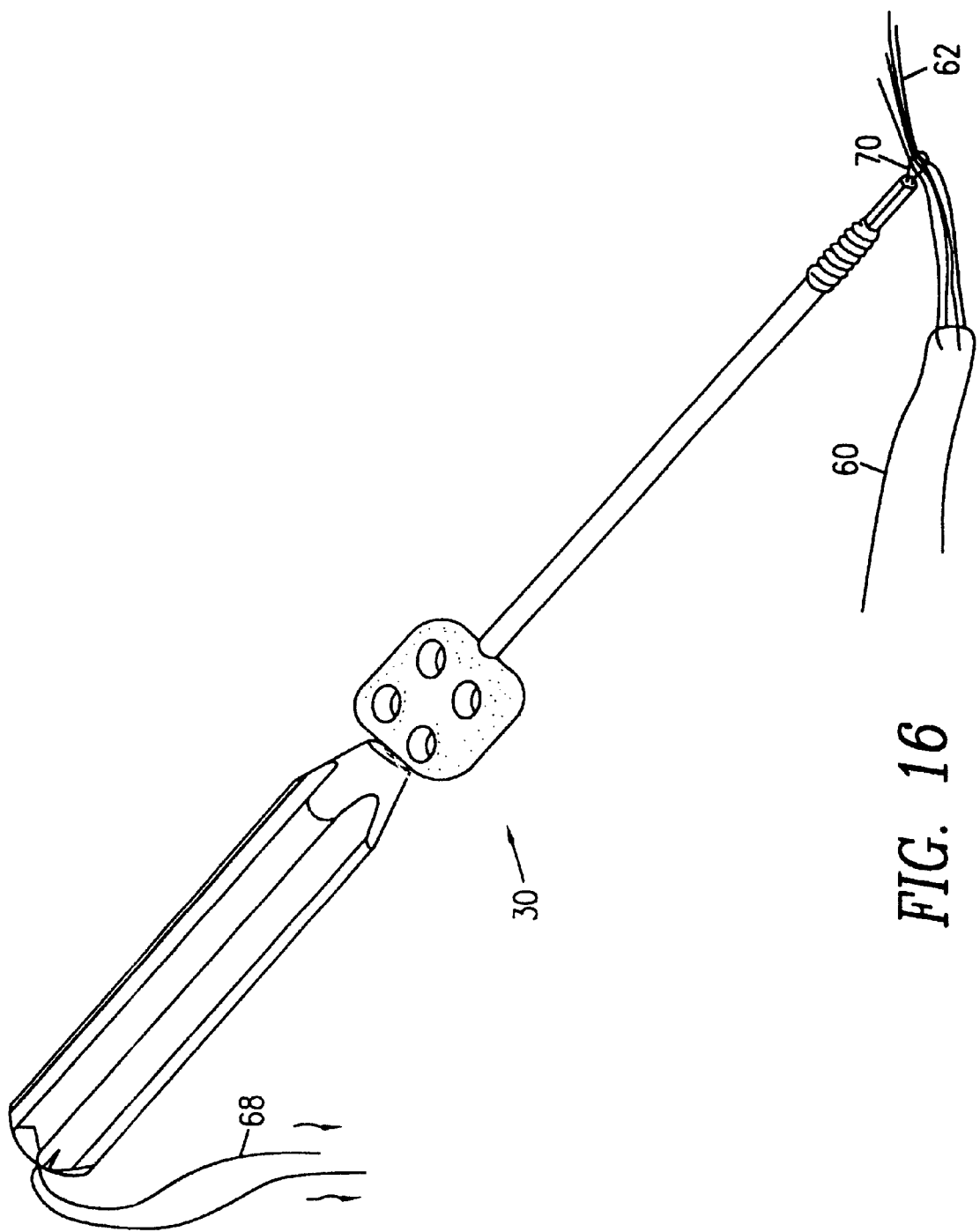
FIG. 16 illustrates the sutures attached to the graft being passed through the suture loop according to the present invention.

Next, as shown in FIG. 15, driver 30 is pre-loaded with screw 10 with outer shaft 36 in the fully retracted position and the distal end of the screw abutting shoulder 37 of inner shaft 34 and the distal end surface of outer shaft 36. Traction suture 68 is passed into the cannula of the driver, such that a looped end 70 is exposed at the distal end of the driver. Sutures 62 attached to graft 60 are then passed through traction suture loop 70 at the end of driver 30 as seen in FIG. 16, to position the graft at an appropriate distance from the distal end of driver 30, either at a distance corresponding to the length of the screw or so that the graft is located directly at the distal end of the driver.

Figure 17:
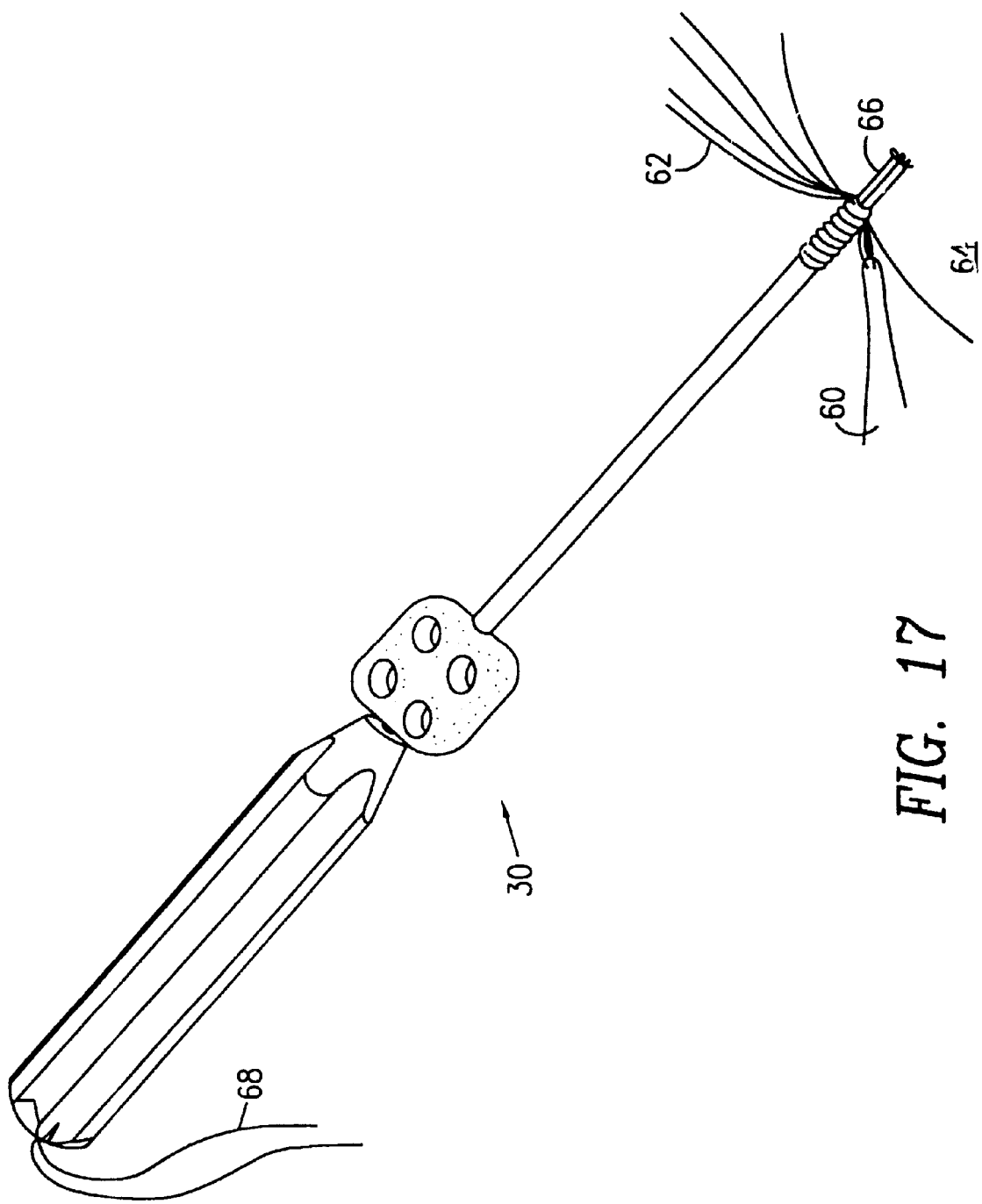
FIG. 17 is a view through a cross-section of the bone socket which shows the sutures attached to the graft being held in contact with the bottom of the bone socket with the interference screw positioned just out of the socket.
Figure 18A:
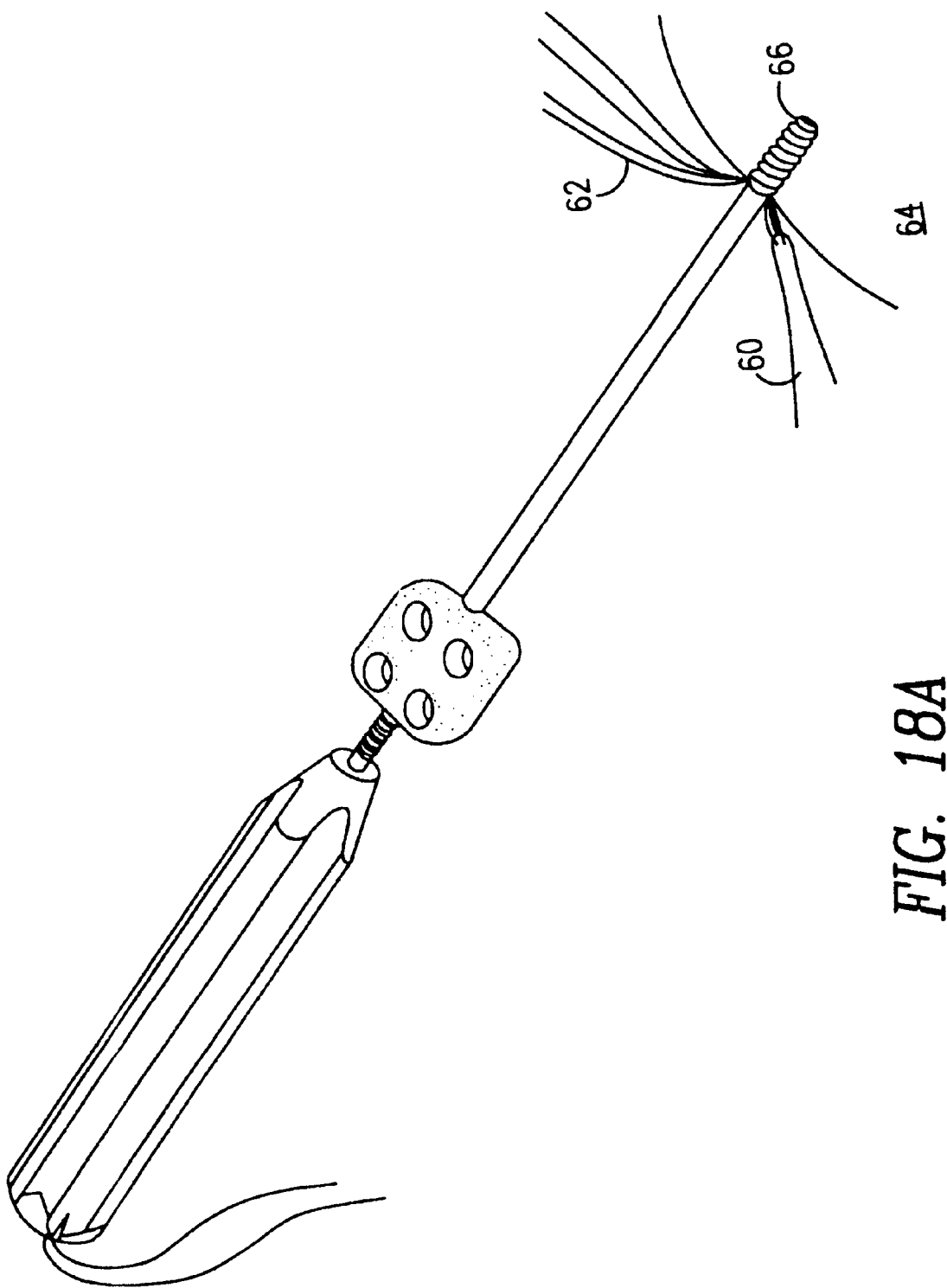
FIG. 18A is a view through a cross-section of the bone through the socket.
Figure 18B:
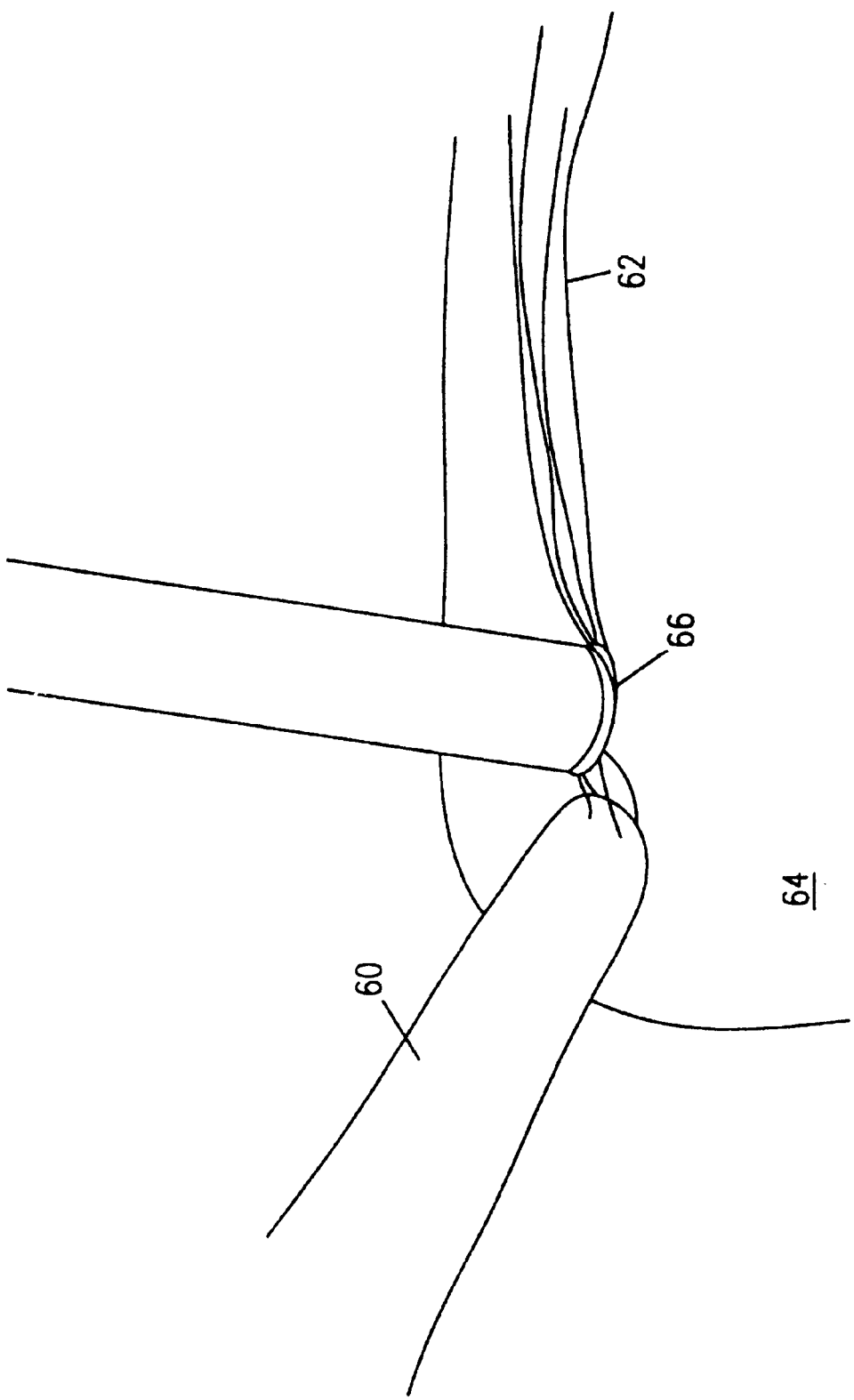
FIG. 18B illustrates the same step of the invention as shown in FIG. 18A, but provides a close-up view from the surgeon's perspective.

Referring now to FIG. 17, the driver 30 is held with gentle pressure with the distal end of hex section 35 at the bottom of the hole 66, keeping the screw 10 just outside the hole. Tension can then be placed on the graft sutures 62 by drawing on traction suture 68 to tighten suture loop 70. Once adequate tension is achieved on the sutures, the driver is manipulated so that the first thread edge of the screw engages the bone at the edge of the hole 66. The driver is turned by rotating handle 32 and thus inner shaft 34 while preventing outer shaft 36 from rotating by holding thumb pad 41 in place during rotation of handle 32. This maneuver causes the outer shaft to move distally along the inner shaft by the interaction of the inner threads in the outer shaft 62 with the threads on threaded portion 39 of inner shaft 34, while also causing the screw threads to engage the sides of the hole and pull the screw into the hole. The inner shaft of the driver thus rotates without advancing further into the hole, while the outer shaft guides the insertion of the screw into the socket. In this manner, the screw advances along the hex section of the driver until the screw is fully installed to the position shown in FIGS. 18A and 18B, with sutures 62 or the graft 60 pinned and/or wound between the base and sidewall of socket 66 and interference screw 10. Optionally, sutures 62 may be twisted together at the time they are passed through loop 70 to increase contact with the screw upon insertion of the screw into the socket.

Figure 19:
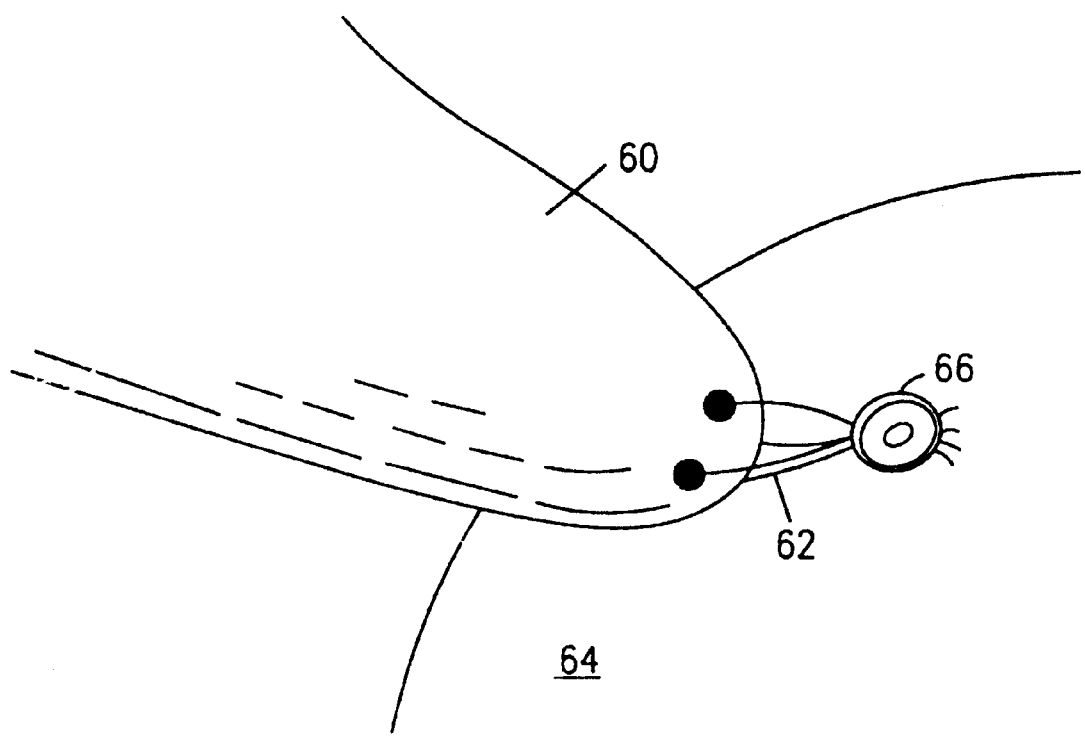
FIG. 19 shows the graft secured to the bone as a result of the method according to the present invention.

After the screw is fully inserted, traction loop 70 is disengaged from the handle, and the driver is removed. As seen in FIG. 19, the ends of the sutures can be removed by clipping them short, leaving the graft securely fastened in place to the bone.

A procedure similar to that just described is performed with respect to the installation of an interference plug, except that a driver such as driver 50 shown in FIGS. 12A and 12B is used instead of driver 30 of FIGS. 7–10, and the plug is advanced into the hole using impact force supplied by a mallet, for example, rather than by turning. When the proximal end of outer shaft 52 is hit with the mallet, the proximal end of plug 20 abutting against shoulder 56 on the inner shaft 54 and the distal surface of outer shaft 52 pushes the plug into the socket 66. In this method, the plug is fully inserted into the hole when the proximal end of outer shaft 52 is flush with the proximal end of inner shaft 54.

In a first alternative to the method described above, sutures 62 attached to the graft 60 are eliminated, so that in the step shown in FIG. 16, the graft itself is passed through the suture loop 70 to be secured from the bottom of the hole 66 by the tip of plug 20.

Figure 20:
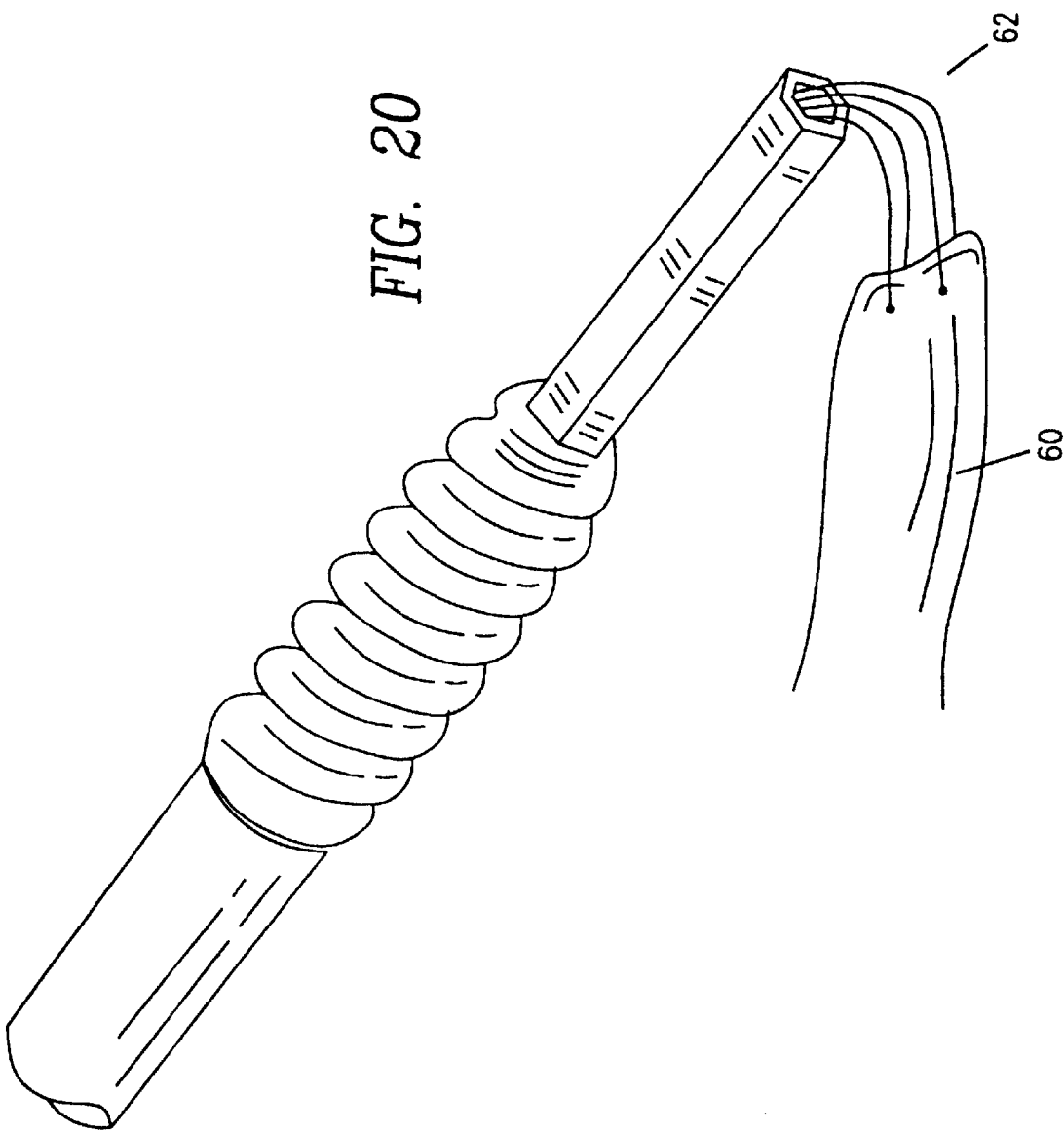
FIG. 20 illustrates an alternative embodiment of the method according to the present invention in which the sutures attached to the graft are threaded directly into and through the driver instead of through a suture loop at the distal end of the driver.

In a second alternative to the method described above, traction suture 68 and loop 70 are eliminated, so that in the step shown in FIG. 16, instead of passing sutures 62 through loop 70, the ends of sutures 62 are threaded into the cannula of the inner shaft 34 through the distal end thereof, through the length of driver 30 or 50, and out the opening at the proximal end thereof, as illustrated in FIG. 20.

A significant advantage provided by the method of the present invention is that the sutures attached to the graft or the graft itself can be securely attached to the bone without the need to tie knots.

Another advantage achieved by the present invention is that the sutures attached to the graft or the graft is secured both along the bottom of the bone socket by the tip of the interference screw or plug, as well as along the sidewall of the socket between the bone and the screw or plug. This arrangement results in a much stronger fixation of the graft to the bone than is achievable with prior art suture anchor procedures.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of soft tissue repair, comprising the steps of:
    forming a hole in a bone at a location at which a soft tissue graft is to be affixed;
    attaching at least one suture to the soft tissue graft to be affixed;
    preloading a cannulated tissue anchor on a tissue anchor driver;
    capturing the suture attached to the graft at a distal end of the driver and inserting the suture into the hole using the driver;
    drawing the soft tissue graft to the hole; and
    installing the cannulated tissue anchor into the hole to secure the suture in the hole by interference-friction fixation between the tissue anchor and the bone forming the hole.

2. The method of graft repair according to claim 1, wherein the interference device is a screw.

3. The method of graft repair according to claim 1, wherein the interference device is one of a wedge or a plug.

4. The method of graft repair according to claim 1, further comprising the step of passing suture through the cannula of the driver such that a loop of suture is exposed at the distal end of the driver, wherein the step of capturing the suture attached to the graft includes:
    feeding the suture attached to the graft through the loop of suture at the distal end of the driver,
    tightening the suture loop, and
    inserting the distal end of the driver into the hole.

5. The method of graft repair according to claim 1, wherein the step of capturing and inserting the suture attached to the graft includes:
    inserting the suture attached to the graft into the cannula of the driver from the distal end thereof,
    feeding the suture through the driver to the proximal end thereof, drawing the graft towards the distal end of the driver by pulling on the at least one suture from the proximal end of the driver, and inserting the distal end of the driver into the hole.

6. The method of graft repair according to claim 1, wherein the driver includes an outer shaft disposed around an inner shaft and movable between a proximal position and a distal position along the inner shaft, and wherein the interference device is loaded onto the inner shaft by inserting the inner shaft through the cannula of the interference device with the outer shaft retracted to the proximal position so that the proximal end of the loaded interference device abuts the distal end of the outer shaft.

7. The method of graft repair according to claim 6, wherein the interference device is a screw having a hex-shaped cannula, a distal portion of the inner shaft of the driver is hex-shaped to be matingly insertable into the hex-chaped interference screw cannula, the inner shaft of the driver is rotatable relative to the outer shaft to move the outer shaft between the proximal and distal positions therealong, and the interference screw is installed by turning the inner shaft to drive the interference screw into the bone while preventing the outer shaft from rotating so that the outer shaft moves distally along the inner shaft to guide the interference screw into the bone.

8. The method of graft repair according to claim 6, wherein the interference device is a plug, the inner shaft of the driver is slidable relative to the outer shaft to move the outer shaft between the proximal and distal positions therealong, and the interference plug is installed by impacting the outer shaft with a mallet until the proximal end of the outer shaft is aligned with the proximal end of the inner shaft, the interference plug being pushed into the bone by the distal end of the outer shaft.

9. A method of soft tissue repair, comprising the steps of:

forming a hole in a bone at a location at which a soft tissue graft is to be affixed;

preloading a cannulated tissue anchor on a tissue anchor driver;

capturing the soft tissue graft at a distal end of the driver and inserting the soft tissue graft into the hole; and inserting the tissue anchor into the hole to secure the soft tissue graft in the hole by interference-friction fixation of the graft between the tissue anchor and the bone forming the hole.

10. The method of graft repair according to claim 9, wherein the tissue anchor is a cannulated interference device, and the method further comprises the steps of:

loading the cannulated interference device onto a cannulated driver;

passing suture through the cannula of the driver to expose a loop of suture at the distal end of the driver; and using the driver to install the interference device into the hole, wherein the step of capturing and inserting the graft includes:

feeding the graft through the loop of suture at the distal end of the driver, tightening the suture loop from the proximal end of the driver, and inserting the distal end of the driver into the hole.

11. The method of graft repair according to claim 10, wherein the interference device is a screw.

12. The method of graft repair according to claim 10, wherein the interference device is one of a wedge or a plug.

13. The method of graft repair according to claim 10, wherein the driver includes an outer shaft disposed around an inner shaft and movable between a proximal position and a distal position along the inner shaft, and wherein the interference device is loaded onto the inner shaft by inserting the inner shaft through the cannula of the interference device with the outer shaft retracted to the proximal position so that the proximal end of the loaded interference device abuts the distal end of the outer shaft.

14. The method of graft repair according to claim 13, wherein the interference device is a screw having a hex-shaped cannula, a distal portion of the inner shaft of the driver is hex-shaped to be matingly insertable into the hex-shaped interference screw cannula, the inner shaft of the driver is rotatable relative to the outer shaft to move the outer shaft between the proximal and distal positions therealong, and the interference screw is installed by turning the inner shaft to drive the interference screw into the bone while preventing the outer shaft from rotating so that the outer shaft moves distally along the inner shaft to guide the interference screw into the bone.

15. The method of graft repair according to claim 13, wherein the interference device is a plug, the inner shaft of the driver is slidable relative to the outer shaft to move the outer shaft between the proximal and distal positions therealong, and the interference plug is installed by impacting the outer shaft with a mallet until the proximal end of the outer shaft is aligned with the proximal end of the inner shaft, whereby the interference plug is pushed into the bone by the distal end of the outer shaft.

16. A method of soft tissue repair, comprising the steps of:

forming a socket in bone at a location at which a soft tissue graft is to be affixed;

preloading a cannulated tissue anchor on a distal end of an anchor driver;

securing the graft to the distal end of the anchor driver and inserting the graft into the socket; and installing the tissue anchor into the opening to secure the graft in the socket by fixation of the graft between the tissue anchor and the bone forming the socket.

17. The method of claim 16, wherein the step of securing the graft comprises passing the graft through a loop disposed at the distal end of the driver.

18. The method of claim 17, wherein the loop is formed of a flexible strand.

19. The method of claim 16, wherein the step of securing the graft comprises capturing suture attached to the graft.

20. The method of claim 16, wherein the step of securing the graft comprises threading suture coupled to the graft into a cannula of the anchor driver.

* * * * *